United States Patent [19]

Givens

[11] 4,434,806
[45] Mar. 6, 1984

[54] DENTAL FLOSS HOLDER

[76] Inventor: James M. Givens, 4929 Collwood Blvd., C-5, San Diego, Calif. 92115

[21] Appl. No.: 385,988

[22] Filed: Jun. 7, 1982

[51] Int. Cl.³ .............................................. A61C 15/00
[52] U.S. Cl. ..................................................... 132/91
[58] Field of Search ................................... 132/91–93; 264/251, 271.1, 249

[56] References Cited

U.S. PATENT DOCUMENTS

| | | | | |
|---|---|---|---|---|
| D. 268,955 | 5/1983 | Givens | | 132/91 |
| 1,955,428 | 4/1934 | Ladwig | | 132/92 R |
| 2,444,638 | 7/1948 | Dobbins | | 132/92 R |
| 2,648,341 | 8/1953 | Moll | | 132/91 |
| 4,280,518 | 7/1981 | Gambaro | | 132/93 |

*Primary Examiner*—Gregory E. McNeill
*Attorney, Agent, or Firm*—Ralph S. Branscomb

[57] ABSTRACT

A dental floss holder is provided which comprises a flattened, somewhat diamond-shaped resilient plastic body with a pair of laterally opposed spring arms and a central tip terminating in a grooved boss, opposite from a pointed spindle which doubles as a tie-down point for the ends of a length of floss and a toothpick. By inserting floss through an aperture in the spindle and stretching it around the lateral arms and the stem terminus, two taut floss segments are defined which can be used simultaneously if desired on the upper and lower teeth.

1 Claim, 7 Drawing Figures

U.S. Patent     Mar. 6, 1984     4,434,806
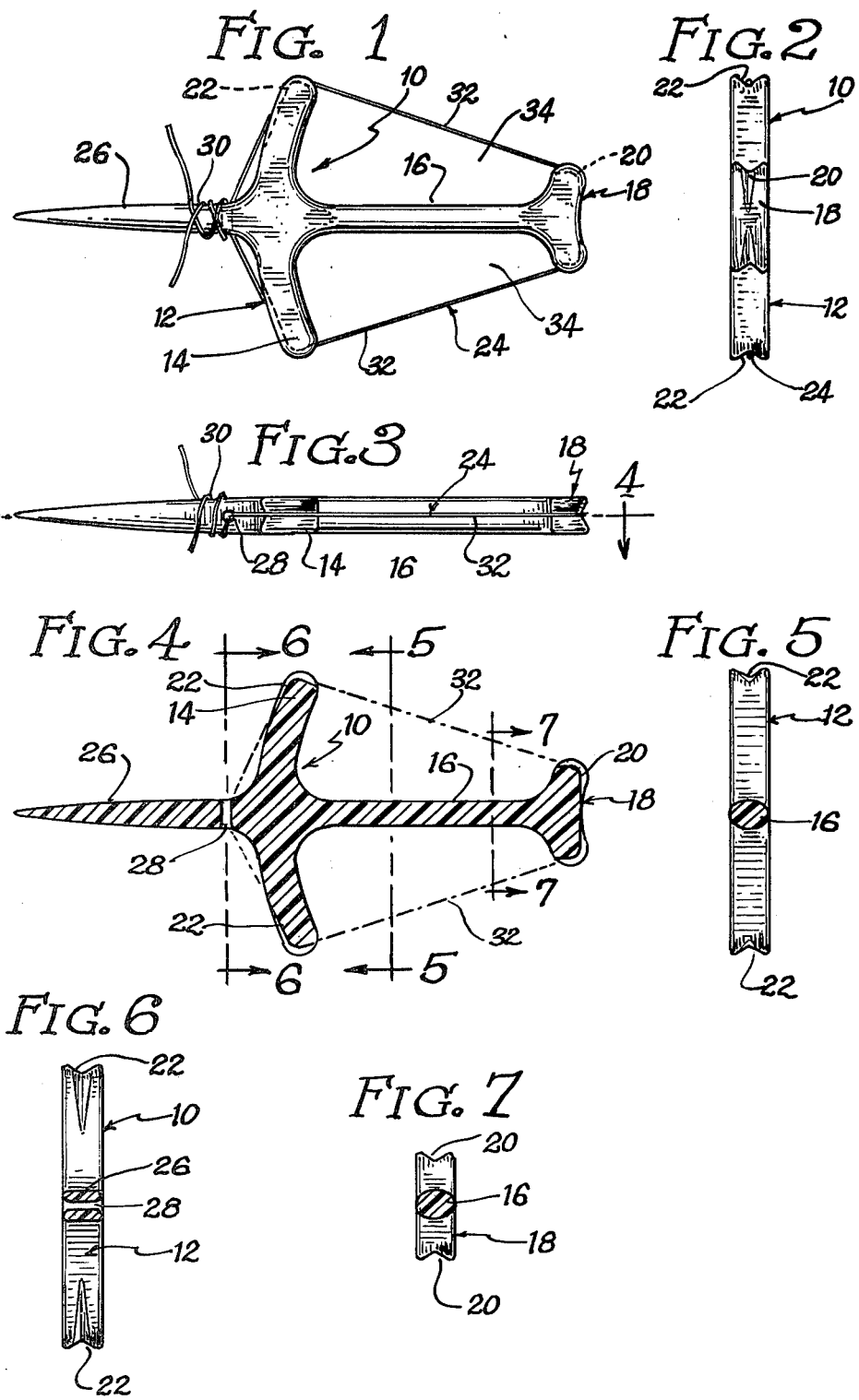

DENTAL FLOSS HOLDER

BACKGROUND OF THE INVENTION

With increased public awareness of the utility of dental floss and maintaining one's native teeth for one's entire life, dozens of different floss holding devices have been developed. Generally speaking, the earlier flossing devices comprised some kind of a central handle that doubled as a container for a roll of floss, with some floss extenders protruding from one end. Typically, some method was provided for stringing the floss out from the central spool in the handle, across the extenders, and back to some tie-down on the handle.

This type of floss holder is somewhat complicated compared to more recently designed units. Although the older style has been successfully marketed, albeit to a somewhat limited market, for years, current interest in floss holding devices has switched to a much simpler device which is not only considerably cheaper to produce, being producible for pennies a unit even in relatively small quantities, but is also much handier and much more likely to be carried around by the purchaser, and thus much more effective in the long run in insuring that proper care is taken of the teeth.

In addition to being much smaller, cheaper, and compact, there is a tendency for more recently designed floss holder to be disposable. Typically, this is achieved by simply molding one or more floss segments directly into the tips of an injected plastic body.

SUMMARY OF THE INVENTION

The present invention combines the advantageous features of the earlier floss units, primarily the ability to re-use the floss spanner body, with features of the newer units, to produce a small, inexpensive unit which can easily fit in a shirt pocket without even being noticeable. This floss holder reduces the whole concept of floss holders to its simpliest and most inexpensive form, whereby additional lengths of floss may be added to the unit from time to time replace used floss, and yet the bulky spool-fed structure is omitted.

Among the advantages and features enumerated in more detail in the specification below, the design of the unit creates a pair of angled, taut floss segments which may be used to floss the upper and lower teeth at the same time. This has an advantage beyond the mere fact that two interdental surfaces can be flossed at the same time. This extra advantage lies in the ease of use of the flosser, because the lower teeth applied against one of the floss segments can pressure the upper segment into the upper interdental surfaces, requiring very little finger pressure. The unit can be held by its tapered spindle, and inserted progressively around the mouth, with the jaw itself exerting the only real force required to flick the floss segments between tooth surfaces.

Thus, whereby traditionally flossing the teeth, especially without some kind of holder, was a rather tedious job requiring some dedication and commitment to one's dental health, by the use of the instant floss holder proper dental care can be accomplished routinely as a nervous habit. Rather than chewing on the end of a pencil or a ballpoint pen to release nervous energy, the owner of the instant pick can instead gnaw on the two floss segments, putting his or her nervous energy to use.

BRIEF DESCRIPTION OF THE DRAWINGS

FIG. 1 is a front elevation view of floss holder;

FIG. 2 is an elevation view from the right end of the floss holder as seen in FIG. 1;

FIG. 3 is a top elevation view of the floss holder;

FIG. 4 is a section taken along line 4—4 of FIG. 3;

FIG. 5 is a section taken along line 5—5 of FIG. 4;

FIG. 6 is a section taken along line 6—6 of FIG. 4;

FIG. 7 is a section taken along line 7—7 of FIG. 4.

DETAILED DESCRIPTION OF THE PREFERRED EMBODIMENT

In its preferred form, the invention comprises a single, resilient body 10, most probably produced in a multiple cavity injection mold. The body defines a crossbar 12, comprised of oppositely directed lateral arms 14 which may be bowed slightly to the right as shown in FIG. 1 to take advantage of the resilience which is incorporated into these arms by the selection of the material used for the body.

A central stem 16, projecting to the right in FIG. 1, terminates in a terminus 18 in the shape of an enlarged boss with a grooved end 20. This groove, as well as groove 22 in the lateral arms, provides corridors for a continuous length of floss 24. The floss is tied through a tie-down spindle 26, preferably through a tie-down aperture 28. By passing both ends of the floss through the hole and twisting, the floss is very easily tensioned. The tip of the spindle is tapered to a point, both to double as a toothpick and to enable the user to spin the holder easily with his index finger and thumb.

The floss is tied down with any suitable kind of knot or overlap at 30, and extends through the grooves 22 on opposite sides of the central stem to form two taut segments 32 of floss defining the outside of large bays 34.

The resilience of the material from which the body 10 is molded causes the segments 32 to be tensioned, and the use of one of the segments will automatically tension the other due to the sliding action of the floss through the corridor in the terminus 18. When the holder is used between the upper and lower teeth, each side acts to help tension the other side, so that no undesirable slack develops.

Although the unit could simply be adapted for use as a disposable, the spindle 26 can still be used as a toothpick and finger spanner, and also serve to wrap enough floss for several uses of the device. The body can be retained indefinitely, or it could be considered a semi-disposable unit, containing enough floss for several fresh wrappings, possibly enough to last a week or two. This feature has a major advantage over simple disposables. For the disposable to be truly effective, the user would have to carry a fresh one at least every day, and possibly two or three a day, if the teeth are flossed after every meal. With the instant holder, however, the user need only replace it with a new one every week or two, making it much more practical and much more likely to be used.

This feature, coupled with the ease with which it can be used between the teeth due to its opposed dual segments and its tapered spindle, makes the unit ideal for practical implementation in the marketplace, for yielding practical oral hygiene benefits on a day to day basis to the user.

While the preferred embodiment of the invention has been described, other modifications may be made thereto and other embodiments may be devised within the spirit of the invention and scope of the appended claims.

What is claimed is:

1. A dental floss holder comprising:
   (a) a crossbar defining a pair of oppositely directed lateral arms;
   (b) a central stem extending generally orthogonally from generally centrally of said crossbar to a terminus;
   (c) a corridor defined in the end of each of said arms and another corridor defined in said terminus for entraining a length of dental floss therethrough such that two lengths span between respective lateral arms and said terminus;
   (d) a tie-down integral with and proximate to said crossbar to tie the ends of length of floss the intermediate portions of which are passed tautly through said corridors;
   (e) said lateral arms extending out well beyond the lateral extent of said terminus such that said two lengths of floss converge together in one direction such that when said strands are engaged between teeth and the respective upper and lower jaws and said holder is reciprocated in a direction axial of said stem, said two strands saw up and down between the teeth;
   (f) said lateral arms, stem, terminus, and tiedown being unitary such that said holder is a one-piece unit;
   (g) said tie-down comprising an apertured spindle extended from the crossbar opposite the direction of said stem to permit tying down floss through the aperture in said spindle, such that said apertured spindle defines said tie-down;
   (h) said spindle being tapered to a point to define a toothpick-projection, and
   (i) said entire holder being symmetrically extended about the axis of said spindle whereby said holder is easily spinnable to encourage the nervous twiddling thereof by the owner; and,
   (j) said lateral arms being resilient and bowed toward said terminal to impart a positive elasticity into said holder and positively tension said two lengths.

* * * * *